(12) United States Patent
Lane (10) Patent No.: US 7,967,857 B2
(45) Date of Patent: Jun. 28, 2011

(54) GASKET WITH SPRING COLLAR FOR PROSTHETIC HEART VALVES AND METHODS FOR MAKING AND USING THEM

(75) Inventor: Ernest Lane, Huntington Beach, CA (US)

(73) Assignee: Medtronic, Inc., Minneapolis, MN (US)

( * ) Notice: Subject to any disclaimer, the term of this patent is extended or adjusted under 35 U.S.C. 154(b) by 573 days.

(21) Appl. No.: 11/668,459

(22) Filed: Jan. 29, 2007

(65) Prior Publication Data

US 2007/0179604 A1      Aug. 2, 2007

Related U.S. Application Data

(60) Provisional application No. 60/743,185, filed on Jan. 27, 2006.

(51) Int. Cl.
*A61F 2/24* (2006.01)
(52) U.S. Cl. .................................................. 623/2.38
(58) Field of Classification Search ........... 623/2.1–2.41
See application file for complete search history.

(56) References Cited

U.S. PATENT DOCUMENTS

| | | | |
|---|---|---|---|
| 3,143,742 A | 8/1964 | Cromie | |
| 3,320,974 A | 5/1967 | High et al. | |
| 3,370,305 A | 2/1968 | Goott et al. | |
| 3,371,352 A | 3/1968 | Siposs | |
| 3,464,065 A | 9/1969 | Cromie | |
| 3,546,710 A | 12/1970 | Ivanovich et al. | |
| 3,571,815 A | 3/1971 | Somyk | |
| 3,574,865 A | 4/1971 | Hamaker | |
| 3,628,535 A | 12/1971 | Ostrowsky et al. | |
| 3,686,740 A | 8/1972 | Shiley | |
| 3,691,567 A | 9/1972 | Cromie | |
| 3,710,744 A | 1/1973 | Goodenough et al. | |
| 3,744,060 A | 7/1973 | Bellhouse et al. | |
| 3,755,823 A | 9/1973 | Hancock | |
| 3,800,403 A | 4/1974 | Anderson | |
| 3,839,741 A | 10/1974 | Haller | |

(Continued)

FOREIGN PATENT DOCUMENTS

CN          2356656          1/2000

(Continued)

OTHER PUBLICATIONS

Lutter, et al., Percutaneous Valve Replacement: Current State and Future Prospects; Ann. Thorac. Surg. 2004;78:2199-2206.

(Continued)

*Primary Examiner* — Suzette J Gherbi
(74) *Attorney, Agent, or Firm* — Katrina A. Witschen; Mike Jaro (57) ABSTRACT

A heart valve prostheses includes an annular member implantable within a biological annulus, a collar extending upwardly from the annular member, and a sewing ring extending from the annular member. A spring structure couples the collar to the annular member and biases the collar to align with the annular member at a predetermined distance above the annular member. During use, the prosthesis is introduced into a biological annulus, and fasteners are directed through the sewing ring into surrounding tissue to secure the prosthesis with the annular member within the biological annulus. A mechanical or bioprosthetic valve is introduced and coupled to the collar, e.g., using tabs or other connectors on the collar. The spring structure allows the collar to be directed towards the annular member and/or folded inwardly, e.g., to facilitate accessing the sewing ring to deliver fasteners.

25 Claims, 6 Drawing Sheets

U.S. PATENT DOCUMENTS

| | | |
|---|---|---|
| 3,959,827 A | 6/1976 | Kaster |
| 3,974,854 A | 8/1976 | Kurpanek |
| 3,996,623 A | 12/1976 | Kaster |
| 3,997,923 A | 12/1976 | Possis |
| 4,035,849 A | 7/1977 | Angell et al. |
| 4,078,268 A | 3/1978 | Possis |
| 4,078,468 A | 3/1978 | Civitello |
| 4,084,268 A | 4/1978 | Ionexcu et al. |
| 4,106,129 A | 8/1978 | Carpentier et al. |
| 4,164,046 A | 8/1979 | Cooley |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,245,358 A | 1/1981 | Moasser |
| 4,259,753 A | 4/1981 | Liotta et al. |
| 4,291,420 A | 9/1981 | Reul |
| 4,297,749 A | 11/1981 | Davis et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,477,930 A | 10/1984 | Totten et al. |
| 4,485,816 A | 12/1984 | Krumme |
| 4,501,030 A | 2/1985 | Lane |
| 4,506,394 A | 3/1985 | Bedard |
| 4,535,483 A | 8/1985 | Klawitter et al. |
| 4,548,202 A | 10/1985 | Duncan |
| 4,605,407 A | 8/1986 | Black et al. |
| 3,409,013 A | 11/1986 | Berry |
| 4,626,255 A | 12/1986 | Reichart et al. |
| 4,629,459 A | 12/1986 | Ionescu et al. |
| 4,665,906 A | 5/1987 | Jervis |
| 4,666,442 A | 5/1987 | Arru et al. |
| 4,680,031 A | 7/1987 | Alonso |
| 4,683,883 A | 8/1987 | Martin |
| 4,687,483 A | 8/1987 | Fisher et al. |
| 4,692,164 A | 9/1987 | Dzemeshkievich et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,743,253 A | 5/1988 | Magladry |
| 4,758,151 A | 7/1988 | Arru et al. |
| 4,775,378 A | 10/1988 | Knoch et al. |
| 4,778,461 A | 10/1988 | Pietsch et al. |
| 4,790,843 A | 12/1988 | Carpentier et al. |
| 4,816,029 A | 3/1989 | Penny, III et al. |
| 4,851,000 A | 7/1989 | Gupta |
| 4,865,600 A | 9/1989 | Carpentier et al. |
| 4,888,009 A | 12/1989 | Lederman et al. |
| 4,892,541 A | 1/1990 | Alonso |
| 4,914,097 A | 4/1990 | Proudian et al. |
| 4,917,698 A | 4/1990 | Carpentier et al. |
| 4,935,030 A | 6/1990 | Alonso |
| 4,960,424 A | 10/1990 | Grooters |
| 4,993,428 A | 2/1991 | Arms |
| 4,994,077 A | 2/1991 | Dobben |
| 5,002,567 A | 3/1991 | Bona et al. |
| 5,010,892 A | 4/1991 | Colvin et al. |
| 5,032,128 A | 7/1991 | Alonso |
| 5,035,708 A | 7/1991 | Wieting et al. |
| 5,037,434 A | 8/1991 | Lane |
| 5,071,431 A | 12/1991 | Sauter et al. |
| 5,104,406 A | 4/1992 | Curcio et al. |
| 5,147,391 A | 9/1992 | Lane |
| 5,163,953 A | 11/1992 | Vince |
| 5,163,954 A | 11/1992 | Curcio et al. |
| 5,163,955 A | 11/1992 | Love et al. |
| 5,178,633 A | 1/1993 | Peters |
| 5,192,303 A | 3/1993 | Gatturna |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,370,685 A | 12/1994 | Stevens |
| 5,376,112 A | 12/1994 | Duran |
| 5,396,887 A | 3/1995 | Imran |
| 5,397,346 A | 3/1995 | Walker et al. |
| 5,397,348 A | 3/1995 | Campbell et al. |
| 5,397,351 A | 3/1995 | Pavcnik et al. |
| 5,406,857 A | 4/1995 | Eberhardt et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,531,784 A | 7/1996 | Love et al. |
| 5,533,515 A | 7/1996 | Coller et al. |
| 5,549,665 A | 8/1996 | Vesely et al. |
| 5,549,666 A | 8/1996 | Hata et al. |
| 5,562,729 A | 10/1996 | Purdy et al. |
| 5,571,175 A | 11/1996 | Vanney |
| 5,571,215 A | 11/1996 | Sterman et al. |
| 5,573,007 A | 11/1996 | Bobo, Sr. |
| 5,573,543 A | 11/1996 | Akopov |
| 5,578,076 A | 11/1996 | Krueger et al. |
| 5,584,803 A | 12/1996 | Stevens et al. |
| 5,607,470 A | 3/1997 | Milo |
| 5,613,982 A | 3/1997 | Goldstein |
| 5,618,307 A | 4/1997 | Donlon et al. |
| 5,626,607 A | 5/1997 | Malecki et al. |
| 5,628,789 A | 5/1997 | Vanney et al. |
| 5,662,704 A | 9/1997 | Gross |
| 5,669,917 A | 9/1997 | Sauer |
| 5,693,090 A | 12/1997 | Unsworth et al. |
| 5,695,503 A | 12/1997 | Krueger et al. |
| 5,713,952 A | 2/1998 | Vanney et al. |
| 5,713,953 A | 2/1998 | Vallana et al. |
| 5,716,370 A | 2/1998 | Williamson, IV et al. |
| 5,716,399 A | 2/1998 | Love |
| 5,720,755 A | 2/1998 | Dakov |
| 5,725,554 A | 3/1998 | Simon |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,807,405 A | 9/1998 | Vanney et al. |
| 5,814,097 A | 9/1998 | Sterman et al. |
| 5,814,098 A | 9/1998 | Hinnenkamp et al. |
| 5,814,100 A | 9/1998 | Carpentier et al. |
| 5,824,060 A | 10/1998 | Christie et al. |
| 5,824,061 A | 10/1998 | Quijano et al. |
| 5,824,064 A | 10/1998 | Taheri |
| 5,830,239 A | 11/1998 | Toomes |
| 5,840,081 A | 11/1998 | Andersen et al. |
| 5,843,179 A | 12/1998 | Vanney et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,603 A | 1/1999 | Reif |
| 5,860,992 A | 1/1999 | Daniel |
| 5,861,028 A | 1/1999 | Angell |
| 5,861,029 A | 1/1999 | Angell |
| 5,865,801 A | 2/1999 | Houser |
| 5,876,436 A | 3/1999 | Vanney et al. |
| 5,879,371 A | 3/1999 | Gardiner et al. |
| 5,891,160 A | 4/1999 | Williamson, IV et al. |
| 5,891,195 A | 4/1999 | Klostermeyer |
| 5,895,420 A | 4/1999 | Mirsch, II et al. |
| 5,902,308 A | 5/1999 | Murphy |
| 5,908,450 A | 6/1999 | Gross et al. |

| | | | |
|---|---|---|---|
| 5,908,452 A | 6/1999 | Bokros et al. | |
| 5,910,170 A | 6/1999 | Reimink et al. | |
| 5,919,147 A | 7/1999 | Jain | |
| 5,921,934 A | 7/1999 | Teo | |
| 5,921,935 A | 7/1999 | Hickey | |
| 5,924,984 A | 7/1999 | Rao | |
| 5,931,969 A | 8/1999 | Carpentier et al. | |
| 5,935,163 A | 8/1999 | Gabbay | |
| 5,957,949 A | 9/1999 | Leonhardt et al. | |
| 5,961,549 A | 10/1999 | Nguyen et al. | |
| 5,961,550 A | 10/1999 | Carpentier | |
| 5,972,004 A | 10/1999 | Williamson, IV et al. | |
| 5,972,024 A | 10/1999 | Northrup, III | |
| 5,976,183 A | 11/1999 | Ritz | |
| 5,984,959 A | 11/1999 | Robertson et al. | |
| 5,984,973 A | 11/1999 | Girard et al. | |
| 6,007,577 A | 12/1999 | Vanney et al. | |
| 6,010,531 A | 1/2000 | Donlon et al. | |
| 6,042,607 A * | 3/2000 | Williamson et al. | 623/2.11 |
| 6,045,576 A | 4/2000 | Starr et al. | |
| 6,059,827 A | 5/2000 | Fenton, Jr. | |
| 6,066,160 A | 5/2000 | Colvin et al. | |
| 6,068,657 A | 5/2000 | Lapeyre et al. | |
| 6,074,041 A | 6/2000 | Gardiner et al. | |
| 6,074,417 A | 6/2000 | Peredo | |
| 6,074,418 A | 6/2000 | Buchanan et al. | |
| 6,081,737 A | 6/2000 | Shah | |
| 6,083,179 A | 7/2000 | Oredsson | |
| 6,096,074 A | 8/2000 | Pedros | |
| 6,099,475 A | 8/2000 | Seward et al. | |
| 6,102,944 A | 8/2000 | Huynh | |
| 6,106,550 A | 8/2000 | Magovern et al. | |
| 6,110,200 A | 8/2000 | Hinnenkamp | |
| 6,113,632 A | 9/2000 | Reif | |
| 6,117,091 A | 9/2000 | Young et al. | |
| 6,126,007 A | 10/2000 | Kari et al. | |
| 6,129,758 A | 10/2000 | Love | |
| 6,139,575 A | 10/2000 | Shu et al. | |
| 6,143,024 A | 11/2000 | Campbell et al. | |
| 6,143,025 A | 11/2000 | Stobie et al. | |
| 6,149,658 A | 11/2000 | Gardiner et al. | |
| 6,162,233 A | 12/2000 | Williamson, IV et al. | |
| 6,165,183 A | 12/2000 | Kuehn et al. | |
| 6,168,614 B1 | 1/2001 | Anderson et al. | |
| 6,176,877 B1 | 1/2001 | Buchanan et al. | |
| 6,183,512 B1 | 2/2001 | Hawanec, Jr. et al. | |
| 6,197,054 B1 | 3/2001 | Hamblin, Jr. et al. | |
| 6,200,306 B1 | 3/2001 | Klostermeyer | |
| 6,203,553 B1 | 3/2001 | Robertson | |
| 6,214,043 B1 | 4/2001 | Krueger et al. | |
| 6,217,610 B1 | 4/2001 | Carpentier et al. | |
| 6,217,611 B1 | 4/2001 | Klostermeyer | |
| 6,231,561 B1 | 5/2001 | Frazier et al. | |
| 6,231,602 B1 | 5/2001 | Carpentier et al. | |
| 6,241,765 B1 | 6/2001 | Griffin et al. | |
| 6,245,102 B1 | 6/2001 | Jayaraman | |
| 6,245,105 B1 | 6/2001 | Nguyen et al. | |
| 6,254,636 B1 | 7/2001 | Peredo | |
| 6,264,691 B1 | 7/2001 | Gabbay | |
| 6,270,526 B1 | 8/2001 | Cox | |
| 6,270,527 B1 | 8/2001 | Campbell et al. | |
| 6,283,127 B1 | 9/2001 | Sterman et al. | |
| 6,283,995 B1 | 9/2001 | Moe et al. | |
| 6,287,339 B1 | 9/2001 | Vazquez et al. | |
| 6,290,674 B1 | 9/2001 | Roue et al. | |
| 6,299,638 B1 | 10/2001 | Sauter | |
| 6,309,417 B1 | 10/2001 | Spence | |
| 6,312,447 B1 | 11/2001 | Grimes | |
| 6,312,465 B1 | 11/2001 | Griffin et al. | |
| 6,319,280 B1 | 11/2001 | Schoon | |
| 6,319,281 B1 | 11/2001 | Patel | |
| 6,322,588 B1 | 11/2001 | Ogle et al. | |
| 6,328,727 B1 | 12/2001 | Frazier et al. | |
| 6,328,763 B1 | 12/2001 | Love et al. | |
| 6,338,740 B1 | 1/2002 | Carpentier | |
| 6,350,281 B1 | 2/2002 | Rhee | |
| 6,358,278 B1 | 3/2002 | Brendzel et al. | |
| 6,358,556 B1 | 3/2002 | Ding et al. | |
| 6,371,983 B1 | 4/2002 | Lane | |
| 6,391,053 B1 | 5/2002 | Brendzel et al. | |
| 6,395,025 B1 | 5/2002 | Fordenbacher et al. | |
| 6,409,759 B1 | 6/2002 | Peredo | |
| 6,413,275 B1 | 7/2002 | Nguyen et al. | |
| 6,419,696 B1 | 7/2002 | Ortiz et al. | |
| 6,425,916 B1 | 7/2002 | Garrison et al. | |
| 6,440,164 B1 | 8/2002 | DiMatteo et al. | |
| 6,447,524 B1 | 9/2002 | Knodel | |
| 6,454,799 B1 | 9/2002 | Schreck | |
| 6,458,153 B1 | 10/2002 | Bailey et al. | |
| 6,461,382 B1 | 10/2002 | Cao | |
| 6,468,305 B1 | 10/2002 | Otte | |
| 6,503,272 B2 | 1/2003 | Duerig et al. | |
| 6,514,265 B2 | 2/2003 | Ho et al. | |
| 6,530,952 B2 | 3/2003 | Vesely | |
| 6,547,827 B2 | 4/2003 | Carpentier et al. | |
| 6,551,332 B1 | 4/2003 | Nguyen et al. | |
| 6,558,418 B2 | 5/2003 | Carpentier et al. | |
| 6,569,196 B1 | 5/2003 | Vesely | |
| 6,582,462 B1 | 6/2003 | Andersen et al. | |
| 6,585,766 B1 | 7/2003 | Huynh et al. | |
| 6,589,279 B1 | 7/2003 | Anderson et al. | |
| 6,598,307 B2 | 7/2003 | Love et al. | |
| 6,602,289 B1 | 8/2003 | Colvin et al. | |
| 6,607,541 B1 | 8/2003 | Gardiner et al. | |
| 6,613,059 B2 | 9/2003 | Ho et al. | |
| 6,613,085 B1 | 9/2003 | Anderson et al. | |
| 6,641,593 B1 | 11/2003 | Schaller et al. | |
| 6,652,578 B2 | 11/2003 | Bailey et al. | |
| 6,676,671 B2 | 1/2004 | Robertson et al. | |
| 6,678,862 B1 | 1/2004 | Love et al. | |
| 6,682,559 B2 | 1/2004 | Myers et al. | |
| 6,685,739 B2 | 2/2004 | DiMatteo et al. | |
| 6,692,513 B2 | 2/2004 | Streeter et al. | |
| 6,695,859 B1 | 2/2004 | Golden et al. | |
| 6,709,457 B1 | 3/2004 | Otte et al. | |
| 6,716,243 B1 | 4/2004 | Colvin et al. | |
| 6,716,244 B2 | 4/2004 | Klaco | |
| 6,716,789 B1 | 4/2004 | Cox | |
| 6,719,790 B2 | 4/2004 | Brendzel et al. | |
| 6,730,118 B2 | 5/2004 | Spenser et al. | |
| 6,733,525 B2 * | 5/2004 | Yang et al. | 623/2.18 |
| 6,764,508 B1 | 7/2004 | Roehe et al. | |
| 6,767,362 B2 | 7/2004 | Schreck | |
| 6,769,434 B2 | 8/2004 | Liddicoat et al. | |
| 6,776,785 B1 | 8/2004 | Yencho | |
| 6,786,924 B2 | 9/2004 | Ryan et al. | |
| 6,786,925 B1 | 9/2004 | Schoon et al. | |
| 6,790,229 B1 | 9/2004 | Berreklouw | |
| 6,790,230 B2 | 9/2004 | Beyersdorf et al. | |
| 6,805,711 B2 | 10/2004 | Quijano et al. | |
| 6,830,585 B1 | 12/2004 | Artof et al. | |
| 6,833,924 B2 | 12/2004 | Love et al. | |
| 6,837,902 B2 | 1/2005 | Nguyen et al. | |
| 6,846,324 B2 | 1/2005 | Stobie | |
| 6,846,325 B2 | 1/2005 | Liddicoat | |
| 6,872,226 B2 | 3/2005 | Cali et al. | |
| 6,893,459 B1 | 5/2005 | Macoviak | |
| 6,893,460 B2 | 5/2005 | Spenser et al. | |
| 6,896,690 B1 | 5/2005 | Lambrecht et al. | |
| 6,908,481 B2 | 6/2005 | Cribier | |
| 6,911,043 B2 | 6/2005 | Myers et al. | |
| 6,913,607 B2 | 7/2005 | Ainsworth et al. | |
| 6,918,917 B1 | 7/2005 | Nguyen et al. | |
| 6,921,407 B2 | 7/2005 | Nguyen et al. | |
| 6,926,730 B1 | 8/2005 | Nguyen et al. | |
| 6,929,653 B2 | 8/2005 | Streeter | |
| 6,939,365 B1 | 9/2005 | Fogarty et al. | |
| 6,945,980 B2 | 9/2005 | Nguyen et al. | |
| 6,945,997 B2 | 9/2005 | Huynh et al. | |
| 6,960,221 B2 | 11/2005 | Ho et al. | |
| 6,974,476 B2 * | 12/2005 | McGuckin et al. | 623/2.36 |
| 7,011,681 B2 | 3/2006 | Vesely | |
| 7,025,780 B2 | 4/2006 | Gabbay | |
| 7,037,333 B2 | 5/2006 | Myers et al. | |
| 7,070,616 B2 | 7/2006 | Majercak et al. | |
| 7,083,648 B2 | 8/2006 | Yu | |
| 7,097,659 B2 | 8/2006 | Woolfson et al. | |
| 7,101,396 B2 | 9/2006 | Artof et al. | |

| Patent/Pub No. | Date | Name |
|---|---|---|
| 7,134,184 B2 | 11/2006 | Schreck |
| 7,141,064 B2 | 11/2006 | Scott et al. |
| 7,147,663 B1 | 12/2006 | Berg et al. |
| 7,153,324 B2 | 12/2006 | Case et al. |
| 7,172,625 B2 * | 2/2007 | Shu et al. .................. 623/2.41 |
| 7,175,659 B2 | 2/2007 | Hill et al. |
| 7,182,769 B2 | 2/2007 | Ainsworth et al. |
| 7,186,265 B2 | 3/2007 | Sharkawy et al. |
| 7,195,641 B2 | 3/2007 | Palmaz et al. |
| 7,201,761 B2 | 4/2007 | Woolfson et al. |
| 7,201,771 B2 | 4/2007 | Lane |
| 7,201,772 B2 | 4/2007 | Schwammenthal et al. |
| 7,214,344 B2 | 5/2007 | Carpentier et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| RE40,377 E | 6/2008 | Williamson, IV et al. |
| 7,393,360 B2 | 7/2008 | Spenser et al. |
| 7,422,603 B2 | 9/2008 | Lane |
| 7,445,632 B2 * | 11/2008 | McGuckin et al. .......... 623/2.37 |
| 7,513,909 B2 * | 4/2009 | Lane et al. ................... 623/2.4 |
| 7,524,330 B2 * | 4/2009 | Berreklouw ................ 623/1.36 |
| 7,547,313 B2 | 6/2009 | Gardiner et al. |
| 7,556,647 B2 | 7/2009 | Drews et al. |
| 7,575,594 B2 * | 8/2009 | Sieracki ......................... 623/2.2 |
| 7,578,843 B2 * | 8/2009 | Shu ............................. 623/2.11 |
| 7,597,711 B2 | 10/2009 | Drews et al. |
| 7,708,775 B2 | 5/2010 | Rowe et al. |
| 7,722,643 B2 | 5/2010 | Ho et al. |
| 7,744,611 B2 | 6/2010 | Nguyen et al. |
| 7,763,040 B2 | 7/2010 | Schaller et al. |
| 7,771,469 B2 | 8/2010 | Liddicoat |
| 2001/0007956 A1 | 7/2001 | Letac et al. |
| 2001/0018592 A1 | 8/2001 | Schaller et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044656 A1 * | 11/2001 | Williamson et al. ......... 623/2.11 |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0055774 A1 | 5/2002 | Liddicoat |
| 2002/0058994 A1 | 5/2002 | Hill et al. |
| 2002/0058995 A1 | 5/2002 | Stevens |
| 2002/0077555 A1 | 6/2002 | Schwartz |
| 2002/0077698 A1 | 6/2002 | Peredo |
| 2002/0091441 A1 | 7/2002 | Nguyen et al. |
| 2002/0116054 A1 | 8/2002 | Lundell et al. |
| 2002/0123802 A1 | 9/2002 | Snyders |
| 2002/0128684 A1 | 9/2002 | Foerster |
| 2002/0138138 A1 | 9/2002 | Yang |
| 2002/0151970 A1 | 10/2002 | Garrison et al. |
| 2002/0173842 A1 | 11/2002 | Buchanan |
| 2002/0177223 A1 | 11/2002 | Ogle et al. |
| 2002/0183834 A1 | 12/2002 | Klaco |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0036791 A1 | 2/2003 | Bonhoeffer et al. |
| 2003/0036795 A1 | 2/2003 | Andersen et al. |
| 2003/0040792 A1 | 2/2003 | Gabbay |
| 2003/0045902 A1 | 3/2003 | Weadock |
| 2003/0055495 A1 | 3/2003 | Pease et al. |
| 2003/0109922 A1 | 6/2003 | Peterson |
| 2003/0109924 A1 | 6/2003 | Cribier |
| 2003/0114913 A1 | 6/2003 | Spenser et al. |
| 2003/0125793 A1 | 7/2003 | Vesely |
| 2003/0130729 A1 | 7/2003 | Paniagua et al. |
| 2003/0149477 A1 | 8/2003 | Gabbay |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0191481 A1 | 10/2003 | Nguyen et al. |
| 2003/0199963 A1 | 10/2003 | Tower et al. |
| 2003/0199971 A1 | 10/2003 | Tower et al. |
| 2003/0229394 A1 | 12/2003 | Ogle et al. |
| 2003/0236568 A1 | 12/2003 | Hojeibane et al. |
| 2004/0015232 A1 | 1/2004 | Shu |
| 2004/0019374 A1 | 1/2004 | Hojeibane et al. |
| 2004/0024452 A1 | 2/2004 | Kruse et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0044406 A1 * | 3/2004 | Woolfson et al. ............ 623/2.11 |
| 2004/0050393 A1 | 3/2004 | Golden et al. |
| 2004/0068276 A1 | 4/2004 | Golden et al. |
| 2004/0078074 A1 | 4/2004 | Anderson et al. |
| 2004/0093075 A1 | 5/2004 | Kuehne |
| 2004/0102797 A1 | 5/2004 | Golden et al. |
| 2004/0106976 A1 | 6/2004 | Bailey et al. |
| 2004/0122514 A1 | 6/2004 | Fogarty |
| 2004/0122516 A1 | 6/2004 | Fogarty |
| 2004/0122526 A1 | 6/2004 | Imran |
| 2004/0167573 A1 | 8/2004 | Williamson, IV et al. |
| 2004/0167620 A1 * | 8/2004 | Ortiz et al. ................... 623/2.11 |
| 2004/0176839 A1 | 9/2004 | Huynh et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0199176 A1 | 10/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0225356 A1 | 11/2004 | Frater |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065601 A1 | 3/2005 | Lee et al. |
| 2005/0065614 A1 | 3/2005 | Stinson |
| 2005/0070924 A1 | 3/2005 | Schaller et al. |
| 2005/0075584 A1 | 4/2005 | Cali |
| 2005/0075659 A1 | 4/2005 | Realyvasquez et al. |
| 2005/0075667 A1 | 4/2005 | Ho et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews |
| 2005/0096738 A1 | 5/2005 | Cali et al. |
| 2005/0098547 A1 | 5/2005 | Cali et al. |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137702 A1 | 6/2005 | Haug et al. |
| 2005/0150775 A1 | 7/2005 | Zhang et al. |
| 2005/0159811 A1 | 7/2005 | Lane |
| 2005/0165477 A1 | 7/2005 | Andruiza et al. |
| 2005/0165479 A1 | 7/2005 | Lane |
| 2005/0182483 A1 | 8/2005 | Osborne et al. |
| 2005/0182486 A1 | 8/2005 | Gabbay |

| | | |
|---|---|---|
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkaway et al. |
| 2005/0216079 A1 | 9/2005 | MaCoviak |
| 2005/0222674 A1 | 10/2005 | Paine |
| 2005/0234545 A1 | 10/2005 | Nugent et al. |
| 2005/0234546 A1 | 10/2005 | Nuget et al. |
| 2005/0240259 A1 | 10/2005 | Sisken et al. |
| 2005/0240263 A1 | 10/2005 | Fogarty |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0004389 A1 | 1/2006 | Nguyen et al. |
| 2006/0005129 A1 | 1/2006 | Damm et al. |
| 2006/0009841 A1* | 1/2006 | McGuckin et al. .......... 623/2.38 |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino |
| 2006/0122692 A1 | 6/2006 | Gilad et al. |
| 2006/0135964 A1 | 6/2006 | Vesely |
| 2006/0136052 A1 | 6/2006 | Vesely |
| 2006/0136054 A1 | 6/2006 | Berg et al. |
| 2006/0149360 A1 | 7/2006 | Schwammenthal et al. |
| 2006/0149367 A1* | 7/2006 | Sieracki ....................... 623/2.21 |
| 2006/0154230 A1 | 7/2006 | Cunanan |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1* | 8/2006 | Lane et al. .................... 623/2.38 |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1* | 11/2006 | Navia et al. ................... 623/2.11 |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1* | 11/2006 | Woolfson et al. ............ 623/2.38 |
| 2006/0276888 A1 | 12/2006 | Lee |
| 2006/0287717 A1 | 12/2006 | Rowe et al. |
| 2006/0287719 A1 | 12/2006 | Rowe et al. |
| 2007/0010835 A1 | 1/2007 | Breton et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0027461 A1 | 2/2007 | Gardiner et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0095698 A1 | 5/2007 | Cambron |
| 2007/0100440 A1 | 5/2007 | Figulla et al. |
| 2007/0106313 A1 | 5/2007 | Golden et al. |
| 2007/0129794 A1 | 6/2007 | Realyvasquez |
| 2007/0142848 A1 | 6/2007 | Ainsworth et al. |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0004696 A1 | 1/2008 | Vesely |
| 2008/0033543 A1* | 2/2008 | Gurskis et al. ............... 623/2.11 |
| 2008/0071361 A1* | 3/2008 | Tuval et al. .................... 623/2.1 |
| 2008/0071369 A1* | 3/2008 | Tuval et al. .................. 623/2.38 |
| 2008/0097595 A1* | 4/2008 | Gabbay ........................ 623/2.42 |
| 2008/0119875 A1 | 5/2008 | Ino et al. |
| 2008/0281411 A1* | 11/2008 | Berreklouw .................. 623/2.11 |
| 2008/0319543 A1 | 12/2008 | Lane |
| 2009/0036903 A1 | 2/2009 | Ino et al. |
| 2009/0054974 A1* | 2/2009 | McGuckin et al. ............ 623/2.1 |
| 2009/0112233 A1 | 4/2009 | Xiao |
| 2009/0177266 A1* | 7/2009 | Powell et al. ................ 623/1.13 |
| 2009/0192529 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2009/0210052 A1* | 8/2009 | Forster et al. ................ 623/2.38 |
| 2009/0264903 A1 | 10/2009 | Lee et al. |
| 2009/0319038 A1 | 12/2009 | Gurskis et al. |
| 2010/0030244 A1* | 2/2010 | Woolfson et al. ............. 606/151 |
| 2010/0044410 A1 | 2/2010 | Argentine et al. |
| 2010/0100174 A1 | 4/2010 | Gurskis |
| 2010/0249894 A1 | 9/2010 | Oba et al. |

FOREIGN PATENT DOCUMENTS

| | | |
|---|---|---|
| DE | 19532973 | 11/1996 |
| EP | 0 084 395 | 8/1986 |
| EP | 0 096 721 | 12/1987 |
| EP | 0 125 393 | 12/1987 |
| EP | 0 179 562 | 7/1989 |
| EP | 1057460 | 12/2000 |
| EP | 1 088 529 | 4/2001 |
| EP | 1171059 | 1/2002 |
| EP | 971 650 | 1/2005 |
| EP | 171 059 | 2/2005 |
| GB | 1093599 | 12/1967 |
| GB | 1477643 | 6/1977 |
| GB | 2011259 | 7/1979 |
| GB | 2 056 023 | 3/1981 |
| GB | 2 069 843 | 9/1981 |
| GB | 2254254 | 10/1992 |
| GB | 2 279 134 | 12/1994 |
| SU | 1116573 | 7/1985 |
| WO | 87/05489 | 9/1987 |
| WO | 89/00084 | 2/1989 |
| WO | 91/15167 | 10/1991 |
| WO | 92/01269 | 8/1992 |
| WO | 92/13502 | 8/1992 |
| WO | 92/19184 | 11/1992 |
| WO | 92/19185 | 11/1992 |
| WO | 95/17139 | 6/1995 |
| WO | 95/28899 | 11/1995 |
| WO | 96/40006 | 12/1996 |
| WO | 97/09933 | 3/1997 |
| WO | 97/09944 | 3/1997 |
| WO | 97/27799 | 8/1997 |
| WO | 97/41801 | 11/1997 |
| WO | 97/42871 | 11/1997 |
| WO | 98/06329 | 2/1998 |
| WO | 99/11201 | 3/1999 |
| WO | 99/15112 | 4/1999 |
| WO | 99/51169 | 10/1999 |
| WO | 00/32105 | 6/2000 |
| WO | 00/40176 | 7/2000 |
| WO | 00/44311 | 8/2000 |

| | | |
|---|---|---|
| WO | 00/56250 | 9/2000 |
| WO | 00/59382 | 10/2000 |
| WO | 00/60995 | 10/2000 |
| WO | 00/64380 | 11/2000 |
| WO | 01/10310 | 2/2001 |
| WO | 01/10312 | 2/2001 |
| WO | 01/58363 | 8/2001 |
| WO | 01/76510 | 10/2001 |
| WO | 01/82840 | 11/2001 |
| WO | 01/87190 | 11/2001 |
| WO | 2004/006810 | 1/2004 |
| WO | 2004/089246 | 10/2004 |
| WO | 2005/004753 | 1/2005 |
| WO | 2005/020842 | 3/2005 |
| WO | 2005/039452 | 5/2005 |
| WO | 2005/072655 | 8/2005 |
| WO | 2006/086135 | 8/2006 |
| WO | 2009/137517 | 11/2009 |

OTHER PUBLICATIONS

Jansen, et al., "Detachable Shape-Memory Sewing Ring for Heart Valves," Artif. Organs. vol. 16, No. 3, 1992, pp. 294-297, Helmholtz Institute for Biomedical Engineering, Technical University of Aachen, Aachn, Germany.

* cited by examiner

GASKET WITH SPRING COLLAR FOR PROSTHETIC HEART VALVES AND METHODS FOR MAKING AND USING THEM

RELATED APPLICATION DATA

This application claims benefit of provisional application Ser. No. 60/743,185, filed Jan. 27, 2006, the entire disclosure of which is expressly incorporated herein by reference.

FIELD OF THE INVENTION

The present invention relates generally to heart valves that may be implanted within a patient, and, more particularly, to multiple component heart valve assemblies, and to apparatus and methods for making and using them.

BACKGROUND

Prosthetic heart valves can replace defective human valves in patients. For example, one piece valves have been suggested that include sewing rings or suture cuffs that are attached to and extend around the outer circumference of a prosthetic valve. In addition, multiple component valves have also been suggested that include a sewing ring that is separate from a valve component. The sewing rings of either type of prosthetic valve can be tedious and time consuming to secure within a target site, i.e., within an annulus of a heart where a natural heart valve has been removed.

For example, to implant a sewing ring within an annulus of a heart, between twelve and twenty sutures may be secured initially to tissue surrounding the annulus. The sewing ring and/or the entire prosthetic valve may then be advanced or "parachuted" down the sutures into the annulus. Knots may then be tied with the sutures to secure the sewing ring within the annulus, whereupon the sutures may be cut. Consequently, this procedure can be very complicated, requiring management and manipulation of many sutures. The complexity of the procedure also provides a greater opportunity for mistakes and requires a patient to be on cardiopulmonary bypass for a lengthy period of time.

Because the annulus of the heart may not match the circular cross-section of the sewing ring and/or prosthetic valve, the prosthetic valve may not fit optimally within the annulus. As a result, natural blood hemodynamics through and around the valve may be impaired, resulting in clotting, possible emboli production, and eventual calcification of the valve structure.

To address this concern, flexible sewing rings have been suggested for use with multiple component valves. The sewing ring may be implanted within the annulus, e.g., using the procedure described above, i.e., parachuted down an arrangement of sutures. The sewing ring may conform at least partially to the anatomy of the annulus. Alternatively, instead of using sutures, it has also been suggested to drive staples through the sewing ring into the surrounding tissue to secure the sewing ring.

When a mechanical or other prosthetic valve is then attached to the sewing ring, however, the valve and sewing ring may not mate together effectively, e.g., if the shape of the sewing ring has been distorted to conform to the annulus, which may also impair natural blood hemodynamics, create leaks, and/or otherwise impair performance of the prosthetic valve.

SUMMARY OF THE INVENTION

The present invention is directed to heart valves that may be implanted within a patient, and, more particularly, to multiple component heart valve assemblies, and to apparatus and methods for making and using them.

In accordance with one embodiment, a prosthesis is provided for receiving a prosthetic valve to replace a preexisting natural or prosthetic heart valve within a biological annulus adjacent a sinus cavity. The prosthesis may include an annular member implantable within the biological annulus, a collar extending upwardly from the annular member, and a sewing ring extending radially outwardly from at least one of the annular member and the collar. The collar and/or annular member may be resiliently compressible, expandable, and/or otherwise movable relative to one another. For example, the collar may be biased to a predetermined orientation, e.g., substantially aligned with a longitudinal axis of the annular member, yet may be compressible axially towards the annular member and/or movable transversely relative to the longitudinal axis.

In accordance with another embodiment, a prosthesis is provided for receiving a prosthetic valve to replace a preexisting natural or prosthetic heart valve within a biological annulus adjacent a sinus cavity. The prosthesis may include an annular member implantable within the biological annulus for contacting tissue surrounding the biological annulus, a collar for engaging with a prosthetic valve, and a spring structure for supporting the collar away from the annular member, e.g., along a longitudinal axis. For example, the spring structure may allow the collar to be compressed towards the annular member along the longitudinal axis and/or transversely relative to the longitudinal axis, yet be resiliently biased to a predetermined position away from the annular member. Optionally, the prosthesis may include a sewing ring, e.g., extending radially outwardly from at least one of the collar and the annular member. The spring structure may also allow the collar to be deflected, folded, and/or compressed transversely relative to the longitudinal axis, e.g., to facilitate accessing the sewing ring and/or annular member during implantation.

In accordance with still another embodiment, a heart valve assembly is provided for implantation within a biological annulus. The heart valve assembly may include an annular prosthesis that includes an annular member implantable within a biological annulus, a collar extending upwardly from the annular member, and a spring structure for supporting the collar away from the annular member, e.g., along a longitudinal axis of the annular member. The heart valve assembly also includes a prosthetic valve, e.g., a mechanical or bioprosthetic heart valve, which may have a circular or multiple lobular shape for implantation above the biological annulus.

Optionally, one or more connectors may be provided on at least one of the collar and the prosthetic valve for securing the prosthetic valve to the annular prosthesis. For example, the one or more connectors may include a plurality of tabs or detents, a drawstring, and the like on the collar for engaging a frame of the prosthetic valve. Alternatively, the one or more connectors may include one or more latches, detents, interlocking elements, e.g., on the prosthetic valve and/or the annular prosthesis.

In one embodiment, the collar may include a plurality of tabs that capture a portion of a frame of the prosthetic valve when the prosthetic valve is directed into engagement with the collar. Optionally, the tabs may be movable, e.g., using a tool, to release the prosthetic valve from the collar.

In exemplary embodiments, the collar, annular member, spring structure, and/or sewing ring may be formed from resiliently flexible material, e.g., metal, such as Nitinol, Elgiloy, or stainless steel, an elastomer, such as silicone, or other plastic material, and may be covered at least partially with a fabric covering. The collar, annular member, and/or spring structure may be formed as a unitary piece or may be separate components that are attached to one another, e.g., before or after being covered with fabric.

In accordance with yet another embodiment, a method is provided for implanting a prosthetic heart valve assembly within a biological annulus, e.g., adjacent a sinus cavity. An annular member may be introduced into the biological annulus, e.g., to direct tissue surrounding the biological annulus outwardly and/or to at least partially dilate the biological annulus. A flexible sewing ring may extend around the annular member that may receive one or more connectors, e.g., sutures, clips, and the like, to secure the annular member relative to the annulus.

In one embodiment, a collar or stand-off extends upwardly from the annular member for receiving the prosthetic valve. The collar may be coupled to the annular member by a spring structure, which may bias the collar to a predetermined position relative to the annular member, but allow the collar to be moved relative to the annular member. For example, the collar may be folded or otherwise moved transversely to facilitate access to the sewing ring, e.g., for directing one or more connectors through the sewing ring. In addition, the collar may be compressible towards the annular member, but resiliently biased to direct the collar upwardly, e.g., within the sinus cavity above the biological annulus.

A prosthetic valve, e.g., a mechanical or bioprosthetic valve, may be advanced into the sinus cavity, and secured relative to the annular member. For example, the prosthetic valve may be secured to the collar using one or more connectors, e.g., a plurality of tabs or detents on the collar, a drawstring in the collar, one or more sutures, clips, detents, and/or other cooperating connectors, e.g., on the collar and/or frame of the valve prosthesis.

The collar may support the prosthetic valve above the tissue biological, e.g., within the sinus cavity, e.g., the sinus of Valsalva above an aortic valve site. In addition or alternatively, the collar may allow the prosthetic valve to have a larger size than the annular member, thereby enhancing the fluid flow or other performance characteristics of the implanted heart valve assembly. Optionally, the collar may include a funnel or other tapered shape that may provide a transition from a relatively larger prosthetic valve to the annular member within the biological annulus. In addition, the collar may support the prosthetic valve away from a wall of the sinus or other supra-annular space, while still allowing blood to flow easily into the coronary arteries around the prosthetic valve.

In another option, the prosthetic valve may be removable from the collar, e.g., to allow the prosthetic valve to be replaced. In addition or alternatively, the collar and prosthetic valve may have a substantially circular shape, which may allow the prosthetic valve to be secured to the collar, yet be rotatable relative to the collar.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION

Turning to the drawings, FIGS. 1-5 show an exemplary embodiment of a heart valve assembly 10 that generally includes a gasket member 12 and a valve member 14. Generally, the gasket member 12 includes an annular ring 18, a sewing ring 20 extending radially from the annular ring 18, and a collar 22 extending upwardly from the annular ring 18. The valve member 14 may be a prosthetic valve, e.g., a mechanical or bioprosthetic valve, that may be secured to the collar 22 and/or other portion of the gasket member 12, e.g., after implanting the gasket member 12 within a tissue annulus, as described further elsewhere herein.

Figure 4:
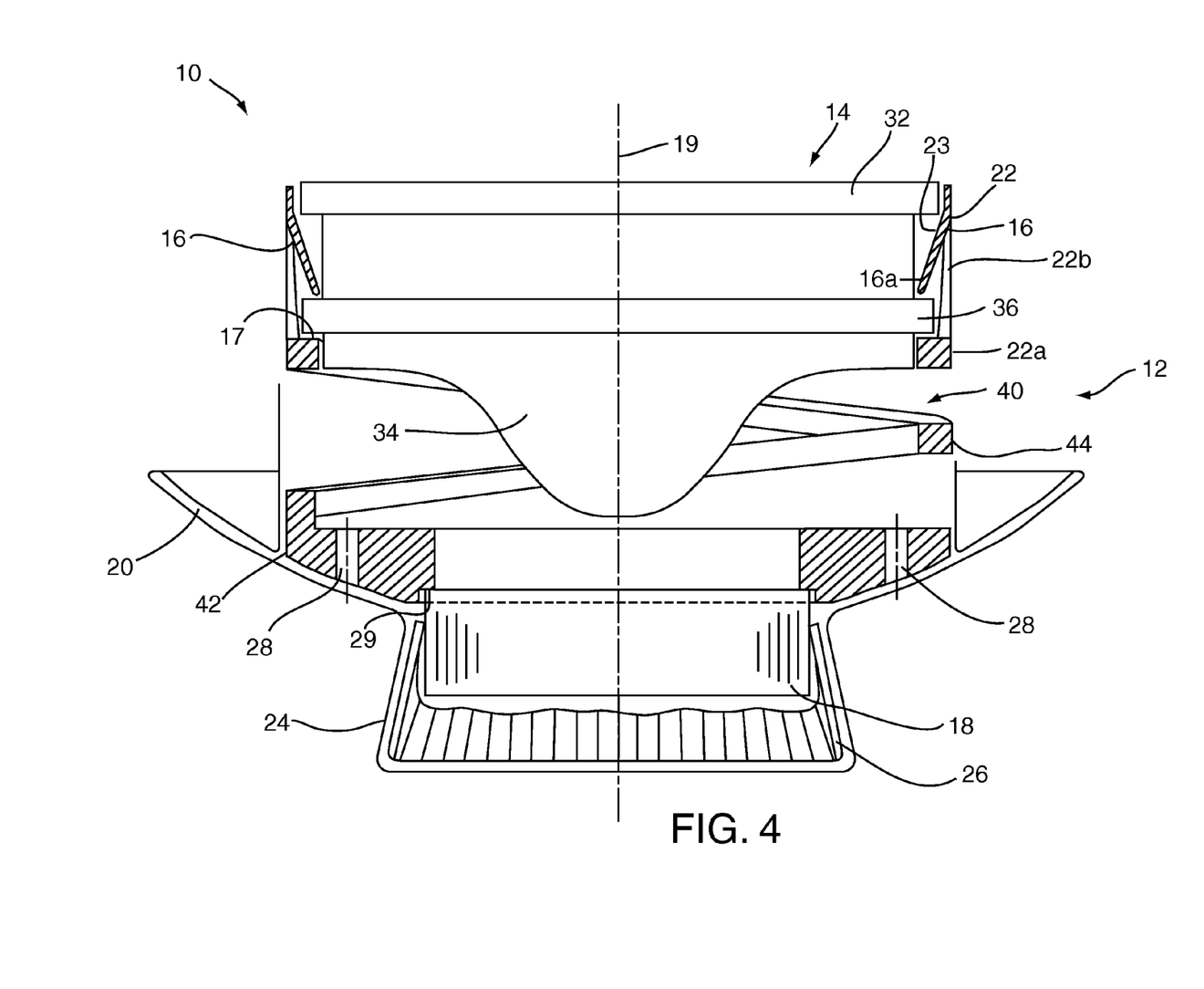
FIG. 4 is a perspective view of a two piece heart valve assembly including a gasket member of FIG. 1 and a mechanical valve.
Figure 5:
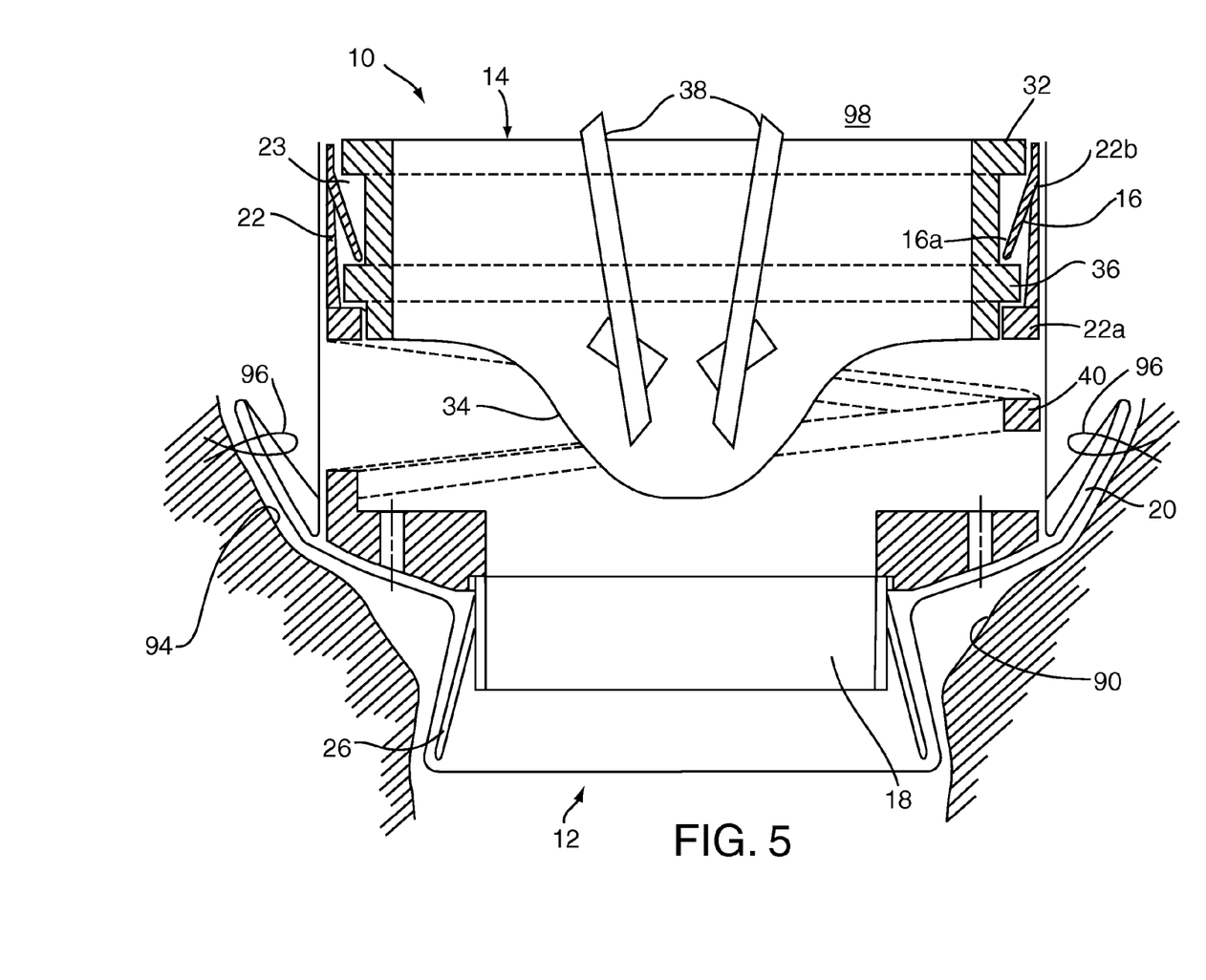
FIG. 5 is a cross-sectional view of an aortic valve site, having the heart valve assembly of FIG. 4 implanted therein.

Turning to FIGS. 4 and 5, the valve member 14 may be a mechanical valve including an annular frame 32 supporting a pair of valve members 38 (shown in FIG. 5) that open and close within the frame 32. Optionally, the valve member 14 may include a pair of ears 34 extending downwardly from the frame 32, e.g., for pivotally supporting the valve members 38. In an exemplary embodiment, the valve member 14 may be a mechanical valve, such as the "Regent" Bileaflet Valve manufactured by St. Jude Medical. In alternative embodiments, the valve member 14 may be another mechanical or bioprosthetic valve, such as those disclosed in U.S. Pat. No. 6,371,983 or U.S. Publication Nos. 2005/0043760, 2006/0235508, or 2006/0276888, the entire disclosures of which are expressly incorporated by reference herein.

Returning to FIGS. 1 and 2, an exemplary embodiment of the gasket member 12 is shown that includes an annular ring 18, a sewing ring 20, a collar 22, and a spring structure 40 supporting the collar 22 relative to the annular ring 18. Fabric 24 may cover all or at least a portion of the gasket member 12, e.g., the annular ring 18, the sewing ring 20, the collar 22, and/or the spring structure 40, for example, to allow tissue ingrowth and/or provide desired flexibility, similar to embodiments described in US Publication Nos. 2004/0122516, 2005/0165479, 2006/0195184, and 2007/0016285, the entire disclosures of which are expressly incorporated by reference herein.

In one embodiment, the annular ring 18 may have a generally circular shape, e.g., defining a central longitudinal axis 19. Alternatively, the annular ring 18 may have a multi-lobular shape about its circumference, e.g., including three lobes separated by scallops or cusps (not shown). In addition or alternatively, the annular ring 18 may generally define a plane substantially perpendicular to the axis 19 or may have a sinusoidal or other shape that extends above and below a plane.

Optionally, the annular ring 18 may be expandable and/or contractible such that the diameter may be adjusted. In one embodiment, the annular ring 18 may be biased to expand to a predetermined diameter. If desired, the annular ring 18 may be contracted radially to a smaller diameter, e.g., folded or compressed to facilitate delivery into a biological annulus, yet may be resiliently expandable to the predetermined diameter, e.g., to dilate tissue surrounding the biological annulus and/or to facilitate securing the gasket member 12 within the biological annulus.

Figure 2:
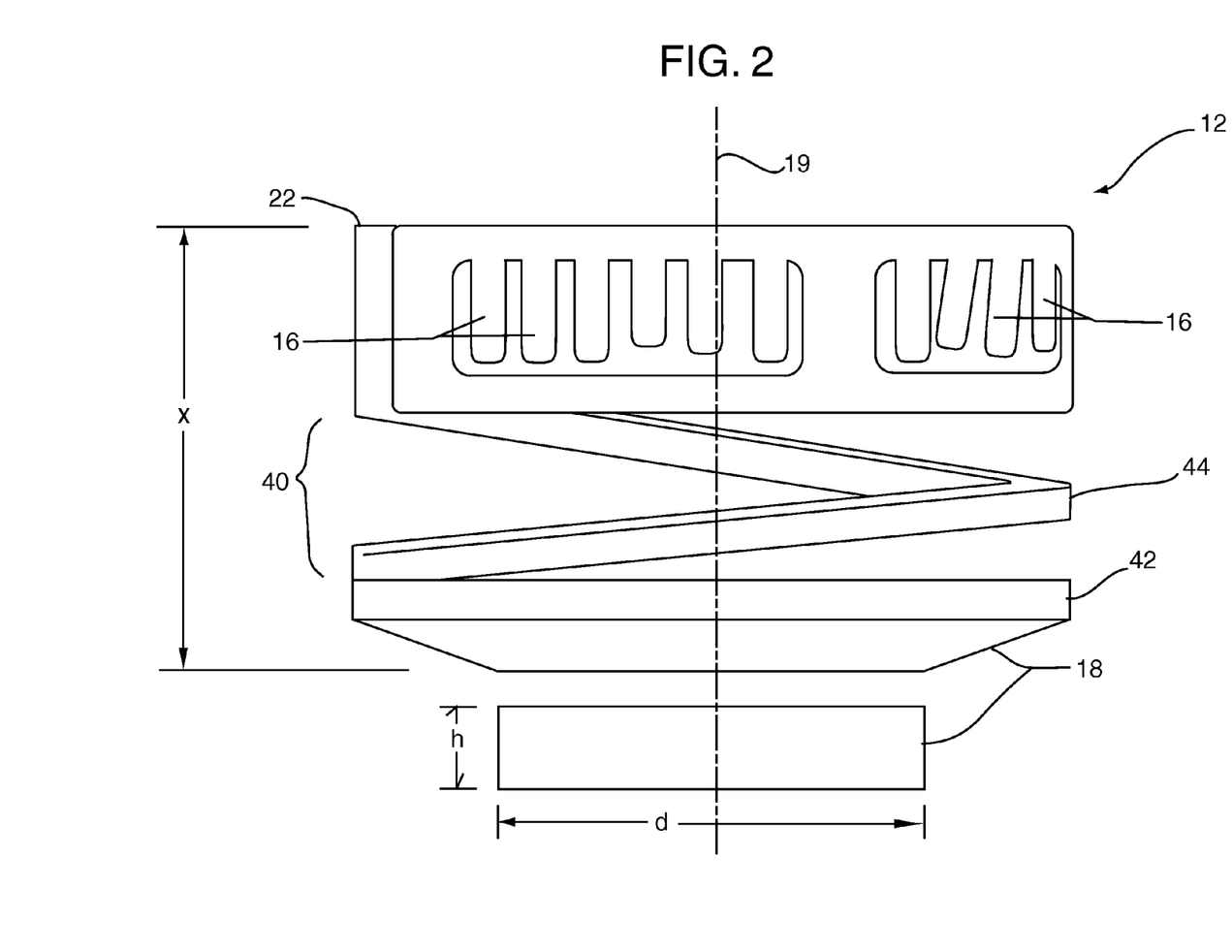
FIG. 2 is a side view of a collar including a spring structure and an annular ring that may be provided in the gasket member of FIG. 1.

The annular ring 18 may be formed from an elastic or superelastic material, e.g., metal such as Nitinol, Elgiloy, stainless steel, and the like, a polymer or other plastic, and/or a composite material. In an exemplary method, the annular ring 18 may be cut from a flat sheet of base material having a desired thickness for the annular ring 18, e.g., by laser cutting, mechanical cutting, and the like. For example, the annular ring 18 may be initially formed as a long band of material (not shown), having a width corresponding to the desired height "h" of the annular ring 18 and a length corresponding to a circumference ($\pi$ d) of the desired diameter "d" of the annular ring 18, as shown in FIG. 2. The band may be wrapped around a mandrel or otherwise restrained in a generally cylindrical shape with the ends adjacent to one another, and the band may be heat treated or otherwise processed to program the generally cylindrical shape to create the annular ring 18. The generally cylindrical shape may include the ends overlapping one another, spaced apart from one another to provide an open "C" shape, or attached to one another.

Fabric may be wrapped at least partially around the annular ring 18, while accommodating expansion and contraction of the annular ring 18, if the annular ring 18 is expandable. For example, at least near the ends, the fabric may not be secured to the annular ring 18, while sutures and the like (not shown) may secure the fabric to other portions of the annular ring 18. Alternatively, the entire annular ring 18 may be free to slide within a fabric sleeve (not shown) wrapped around the annular ring 18. Additional information on the construction of the annular ring 18 may be found in the references incorporated by reference elsewhere herein.

The collar 22 may be spaced apart and/or extend upwardly from the annular ring 18. For example, as best seen in FIGS. 2 and 4, the collar 22 may be coupled to the annular ring 18 by the spring structure 40. Generally, the spring structure 40 may allow the collar 22 to be resiliently compressed or otherwise directed towards the annular ring 18, e.g., substantially along the axis 19. In addition or alternatively, the spring structure 40 may allow the collar 22 to be folded, compressed, or otherwise directed inwardly and/or transversely relative to the axis 19, as described further elsewhere herein.

The collar 22 may be a generally circular annular band 22 for receiving or otherwise engaging the valve member 14, e.g., as described further below. In one embodiment, the collar 22 may include a lower rim 22a defining a lip 17 and a sidewall 22b extending upwardly from the rim 22a, thereby defining a recess 23 for receiving the valve member 14 therein. In addition, the collar 22 may include one or more connectors, e.g., a plurality of detents 16, for securing the valve member 14 within the recess 23 and/or otherwise to the collar 22. As shown, the detents 16 include tabs extending downwardly and inwardly from the sidewall 22b, e.g., defining an angle relative to the axis 19. The tabs 16 may be biased inwardly but may be resiliently deflectable outwardly, e.g., during introduction of the valve member 14. Lower, free ends 16a of the tabs 16 may be spaced above the lip 17, e.g., for capturing a portion of the valve member 14 between the rim 22a and the tabs 16, as described further below.

In addition or alternatively, the collar 22 and/or other portion of the gasket member 12 may include one or more connectors in addition to or instead of the detents 16. For example, the collar 22 may include a plurality of fasteners, clips, latches, and the like (not shown) inset within or otherwise attached to the collar 22, e.g., similar to those disclosed in US Publication Nos. 2006/0195184 and 2006/0235508, incorporated by reference above. Alternatively, the gasket member 12 may include a plurality of guide rails or other elongate members (not shown) extending from the collar 22 and/or sewing cuff 20 for guiding the valve member 14 towards the gasket member 12 and/or securing the valve member 14 to the gasket member 12, similar to the elongate members disclosed in Publication No. 2005/0165479, incorporated by reference above, or co-pending application Ser. No. 60/746,038, filed Apr. 29, 2006, the entire disclosure of which is expressly incorporated by reference herein.

Figure 3A:
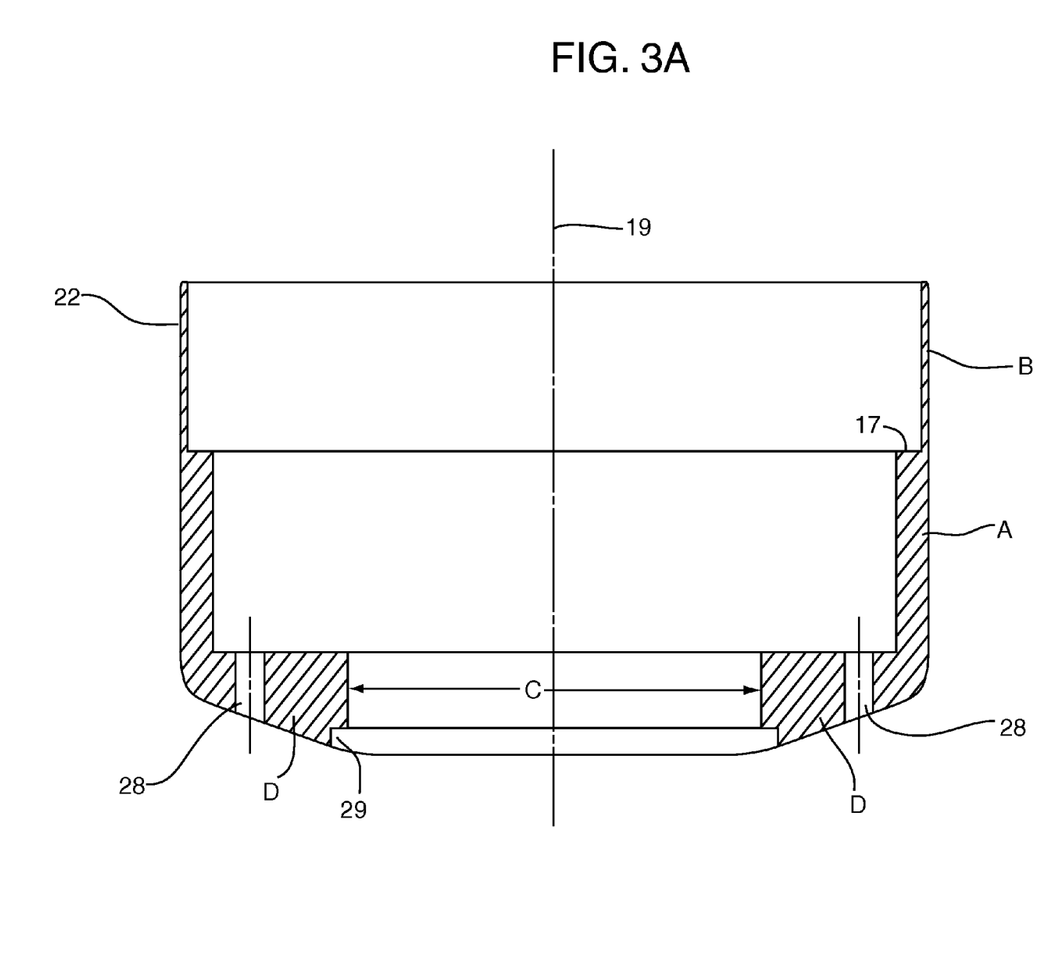
FIG. 3A is a cross-sectional side view of an unfinished blank that may be formed into the collar and spring structure of FIG. 2.

Returning to FIGS. 2-3B, the spring structure 40 may include an annular base 42 and a helically shaped spring member 44 extending upwardly from the base 42, e.g., spiraling around the axis 19. The spring member 44 may be coupled to the collar 22 and the base 42 may be coupled to the annular ring 18. Alternatively, the spring member 44 may be coupled directly to the annular ring 18 and the base 42 may be eliminated (not shown). The spring member 44 may be sufficiently rigid to bias the collar 22 to a predetermined position relative to the annular ring 18. For example, the spring member 44 may bias the collar to align axially above the annular ring 18 along the longitudinal axis 19. In addition or alternatively, the spring member 44 may bias the collar 22 to be spaced a predetermined distance from the annular ring 18, e.g., at a height "x" above the annular ring 18.

As shown, in one embodiment, the base 42 and spring member 44 of the spring structure 40 and the collar 22 may be formed as a unitary piece. For example, the collar 33 and/or spring structure 40 may be formed by machining, molding, casting, stamping, etching, and the like. Alternatively, the base 42, spring member 44, and/or collar 22 may be formed as separate pieces that are attached to one another, e.g., by bonding, sonic welding, cooperating connectors, interference fit, and the like (not shown). Similar to the annular ring 18, the spring structure 40 and/or collar 22 may be formed from metal, such as Nitinol, Elgiloy, stainless steel, and the like, a polymer or other plastic, and/or a composite material. For example, in an alternative embodiment, the spring member 44 may be a metal spring, the base 42 may be formed from silicone or other elastomer (e.g., also providing a core for the sewing ring 20 as well as a base for the spring member 44), and the collar 22 may be formed from Nitinol or other metal attached to the spring member 44.

Figure 3B:
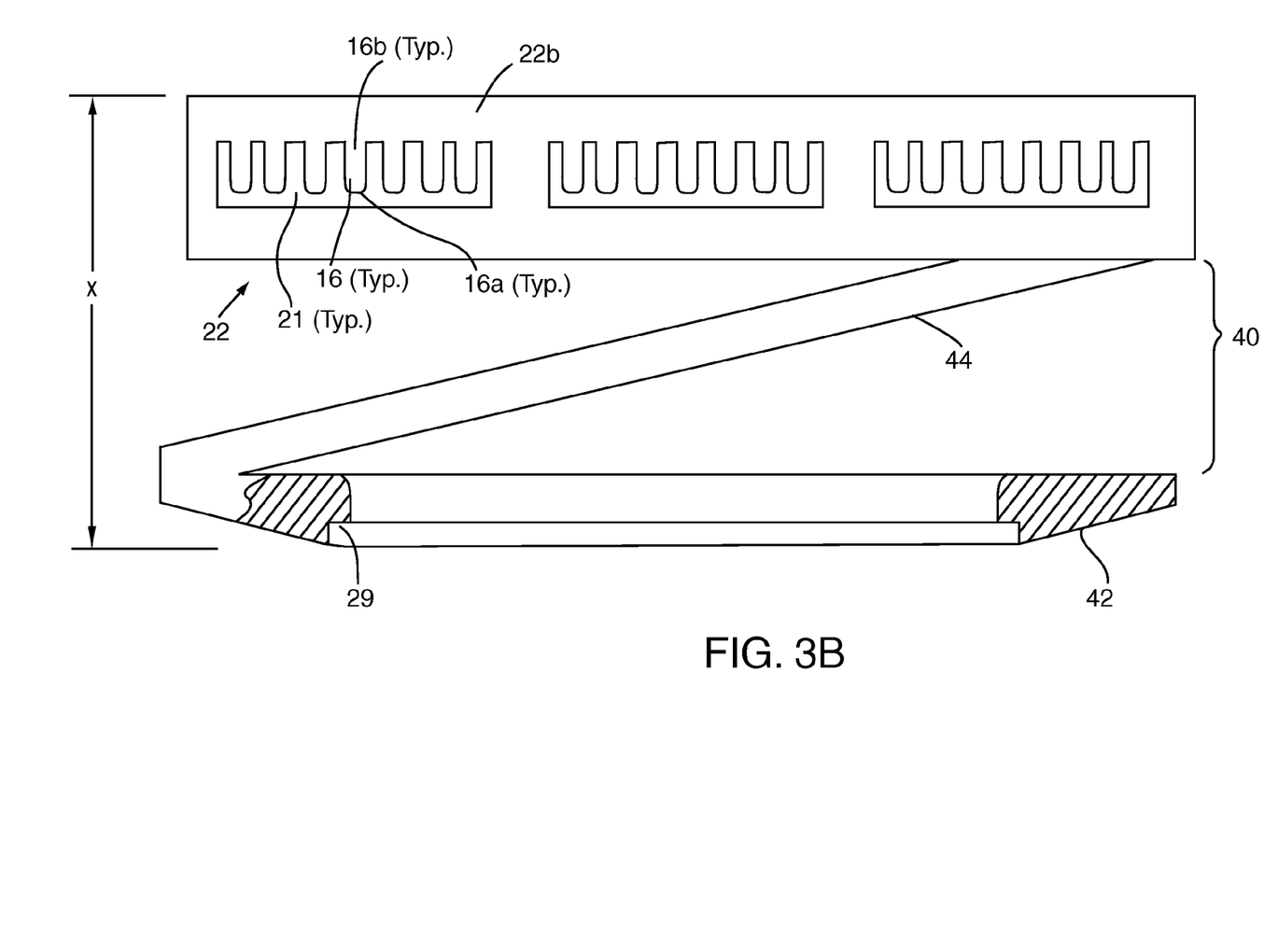
FIG. 3B is a cross-sectional side view of a collar and spring structure formed from the blank of FIG. 3A.

Turning to FIGS. 3A and 3B, in an exemplary embodiment, the collar 22 and spring structure 40 may be formed as a unitary piece from a blank using a laser machining process. Turning to FIG. 3A, a blank may be provided for an unfinished collar 22 that generally includes a lower sidewall section A, an upper sidewall section B, and a base section D, all disposed substantially symmetrically around the longitudinal axis 19. The blank may be formed by machining, molding, casting, and the like from desired materials, e.g., Nitinol, stainless steel, Elgiloy, plastic, and the like. Initially, the blank may have generally cylindrical continuous sidewalls having a greater thickness at section A than at section B, thereby defining lip 17 between sections A and B. The base section D may extend inwardly from section B and may include an opening C therethrough aligned with the longitudinal axis 19, e.g., having a diameter corresponding to the size of the annular ring 18, as seen in FIG. 2. Thus, sections A and B may have a relatively large diameter compared to the opening C.

Optionally, section D may have a tapered or other shape that may conform at least partially to a shape of a biological annulus into which the resulting annular prosthesis 12 is implanted. In addition or alternatively, section D may include a plurality of openings 28 extending therethrough, e.g., for accommodating sutures, staples or other connectors therethrough. The openings C, 28 may be cut, bored, drilled, or otherwise formed through the base 42 or may be created when the base 42 is molded, cast, and the like.

Turning to FIG. 3B, a plurality of tabs 16 may be formed through section A. For example, a plurality of elongate openings 21 may be laser cut (or otherwise created) through section A that extend around the circumference of section A. The remaining material around the openings 21 provides the sidewall 22b of the collar 22 and define a plurality of tabs 16. Thus, the tabs 16 may be fixed at upper ends 16b to the sidewall 22b and may include free lower ends 16a. As shown in FIG. 4, at least some of the tabs 16 may be bent inwardly from the sidewall 22b, e.g., by heat-setting the bent shape, bending the tabs 16 beyond their elastic limit, and the like.

With continued reference to FIGS. 3A and 3B, portions of Section B may be removed, leaving the rim 22b of the collar 22 and the spring member 44. As shown, the spring member 44 may have a height similar to the thickness of Section B, e.g., such that the spring member 44 has a substantially square cross-section. It will be appreciated that other cross-sections may be provided having desired mechanical properties, e.g., a desired spring constant.

Although described in an exemplary order, it will be appreciated that the sequence of the steps described above for forming the collar 22 and spring structure 40 are merely exemplary. The procedure described may be performed in any order, i.e., such that the collar 22, spring member 44, and/or base 42 may be created sequentially or simultaneously with one another.

Optionally, as shown in FIGS. 3A-4, a lower recess 29 may be formed or otherwise provided in the base 42 of the spring structure 40, e.g., around opening C. This recess 29 may be sized to receive an upper edge of the annular ring 18 therein.

Figure 1:
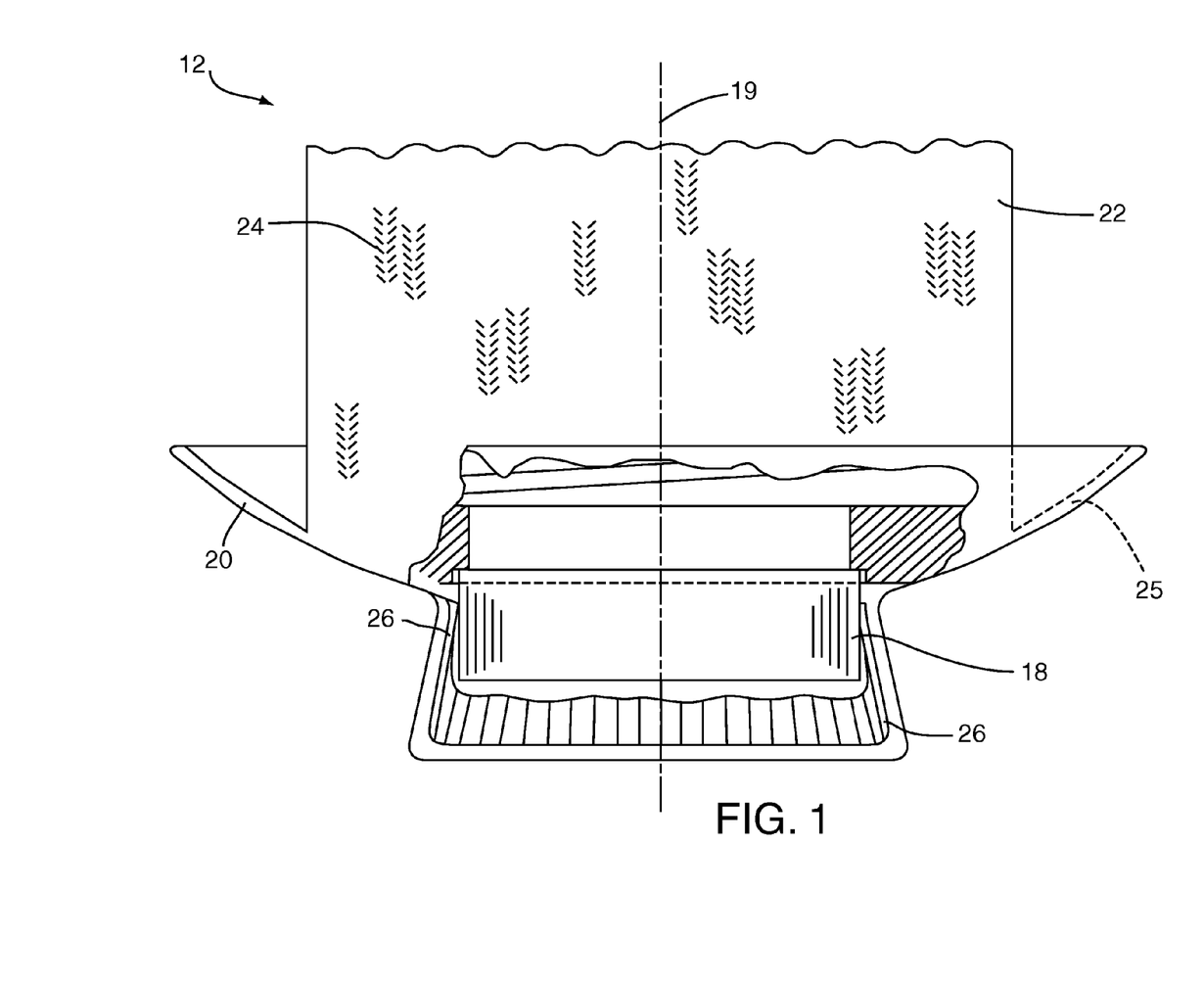
FIG. 1 is a partial cross-sectional side view of an exemplary embodiment of a gasket member with a fabric covering.

With additional reference to FIGS. 1 and 4, the sewing ring 20 may be attached to or otherwise extend around the annular ring 18 and/or spring structure 40. For example, the sewing ring 20 may include one or a plurality of layers of fabric or other material extending radially outwardly from the base 42 and/or the annular ring 18. Alternatively, the sewing ring 20 may include flexible core material 25, e.g., silicone or other elastomeric materials, foam, fabric, felt, polymers, and the like, that may be attached to or otherwise extend around the base 42 and/or annular ring 18, as described in the references incorporated by reference elsewhere herein. Such a core 25 may be molded, fused, bonded, and the like to the base 42 and/or annular ring 18 or may simply be disposed around the base 42 and/or annular ring 18 and held in place by an overlying layer of fabric.

Generally, to make the annular prosthesis shown in FIG. 1, the annular ring 18 may be formed as described above. Optionally, a lower baleen or skirt 26 may be formed that extends downwardly and/or outwardly from the annular ring 18. The skirt 26 may be formed and/or attached to the annular ring 18 as described in the references incorporated by reference elsewhere herein.

The collar 22 and spring structure 40 may be formed as described above, before, after, or in conjunction with the annular ring 18 and/or skirt 26. Once formed, the annular ring 18 may be disposed with the upper edge within the recess 29 within the base 42 of the spring structure 40. Optionally, the annular ring 18 may be attached to the base 42, e.g., by bonding, welding, and the like. Otherwise, the upper edge of the annular ring 18 may simply be placed within the recess 29, and fabric may be wrapped around the annular ring 18 and/or base 42 to hold the annular ring 18 adjacent the base 42. Optionally, one or more sutures (not shown) may be directed through openings (also not shown) in the annular ring 18 and base 42 to secure the annular ring 18 adjacent the base 42.

In an alternative embodiment, the base 42 of the spring structure 40 may be eliminated. In this alternative, the lower end of the spring member 44 may be attached directly to the annular ring 18. For example, the lower end of the spring structure 40 may be bonded, fused, or otherwise attached to an upper region of the annular ring 18.

If the sewing ring 20 includes a core 25, the core 25 may be attached around the base 42 and/or the annular ring 18. The core material may be bonded, molded, or otherwise attached to the base 42 and/or annular ring 18. Fabric may be wrapped or otherwise secured around the core 25, the annular ring 18, the base 42, the spring member 44, and the collar 22, e.g., using known sewing or other methods. The resulting prosthesis 12 shown in FIG. 1 may be entirely covered with fabric (omitted in part only to show the internal components of the prosthesis 12).

As fabric is being secured around the collar 22 and/or spring member 44, the collar 22 may be directed and maintained partially towards the annular ring 18. After securing the fabric, the collar 22 may be released, thereby applying tension on the fabric as the spring member 44 attempts to bias the collar 22 away from the annular member 18. This tension may pull the fabric slightly, e.g., to reduce the risk of the fabric puckering. The fabric may cover the tabs 16 within the collar 22 or openings may be provided in the fabric to allow the tabs to extend therethrough. If the fabric covers the tabs 16, the fabric should not be tensioned to cause the tabs 16 to deflected outwardly from their relaxed position.

Thus, turning to FIG. 4, the resulting annular prosthesis 12 may have a relaxed condition, i.e., free from external forces, in which the collar 22 is spaced apart from the annular ring 18 and/or base 42. The collar 22 may have sufficient height "x" relative to the annular ring 18 to accommodate receiving the frame 32 of the valve member 14 without the ears 34 extending down into the annular ring 18. The collar 22 may include one or more grooves (not shown) formed within the collar 22, which may accommodate the ears 34 of the valve member 14. The collar 22 may have sufficient structural integrity to support the valve member 14, yet be sufficiently flexible to be deformable to facilitate introduction into a patient's body and/or to move the collar 22 away to accommodate delivering one or more connectors (not shown) into the sewing ring 20.

Turning to FIG. 5, during use, the gasket member 12 may be implanted within a patient's body, e.g., within or adjacent to a biological annulus 90. The biological annulus 90 may be the site for replacement of an existing natural or previously implanted heart valve, such as a tricuspid, mitral, aortic, or pulmonary valve within a patient's heart (not shown). With the annular ring 18 contracted into a relatively small diameter (if the annular ring 18 is radially compressible), the gasket member 12 may be advanced into the annulus using a delivery tool (not shown). Exemplary tools, apparatus, and methods for compressing and/or delivering the gasket member 12 are disclosed in co-pending application Ser. No. 60/746,038, filed Apr. 29, 2006, incorporated by reference above.

The gasket member 12 may be advanced until the annular ring 18 extends at least partially into the biological annulus 90. In one embodiment, the annular ring 18 extends entirely through the biological annulus 90, with the lower edge of the annular ring 18 remaining free within the sub-annular space below 92 the biological annulus 90.

Optionally, as shown, the gasket member 12 may include a flexible skirt 26 that extends through the annulus. The skirt 26 may be biased to extend outwardly as shown to provide a smooth transition and/or enhance a seal between the heart vale assembly 10 and the biological annulus.

The sewing ring 20 may contact the tissue within the supra-annular space 94 above the biological annulus 90, although the sewing ring 20 may not provide any structural support of the annular ring 18. For example, the sewing ring 20 may be substantially flexible, e.g., conforming substantially to the shape of the supra-annular space 94.

If the annular ring 18 is expandable or otherwise compressed, the annular ring 18 may then be expanded within the biological annulus 90, e.g., to dilate the biological annulus or otherwise direct the surrounding tissue outwardly against the underlying tissue structures. For example, the annular ring 18 may simply be released by the delivery tool, whereupon the annular ring 18 may resiliently expand against the tissue surrounding the biological annulus 90, thereby substantially securing the annular ring 18 (and consequently, the gasket member 12) relative to the biological annulus 90. In addition or alternatively, a dilation tool (not shown) may be advanced into the gasket member 12 and expanded to forcibly (e.g., plastically) expand the annular ring 18 within the biological annulus 90.

If the sewing ring 20 is restrained by the delivery tool, the sewing ring 20 may be released to allow the sewing ring 20 to contact the surrounding tissue, e.g., within the aortic root above the biological annulus 90. Because of the floppy (i.e., flexible and conformable) nature of the core, the sewing ring 20 may adopt the shape of the surrounding tissue, e.g., lying flatter within the coronary sinus regions, while becoming more vertical adjacent the commissures.

With the gasket member 12 in place, a plurality of fasteners 96, e.g., clips, staples, sutures, and the like, may be directed through the sewing ring 20 into the tissue surrounding the biological annulus 90 to secure the gasket member 12 relative to the biological annulus 90. In addition or alternatively, a plurality of fasteners (not shown) may be directed through the openings 28 in the base 42 to secure the gasket member 12 relative to the biological annulus 90. Exemplary fasteners and apparatus and methods for delivering them are disclosed in U.S. Publication Nos. 2005/0080454 and 2006/0122634, the entire disclosures of which are expressly incorporated by reference herein.

To facilitate accessing the sewing ring 20 during delivery of the fasteners 96, local portions of the collar 22 may be at least partially deflected out of the way. For example, the collar 22 may be folded inwardly to move fabric and other obstructions out of the way, e.g., similar to the embodiments disclosed in U.S. Publication No. 2007/0016285, incorporated by reference herein. Thus, the flexibility of the collar 22 may facilitate visual and/or tactile access to one or more portions of the sewing ring 20, whereupon one or more fasteners 96 may be delivered through the accessed portion(s) of the sewing ring 20. After delivering the fastener(s) 96, the collar 22 may be released, whereupon the collar 22 may resiliently return outwardly to its annular shape.

The valve member 14 may then be advanced into the biological annulus 90, e.g. using another delivery tool or the same tool (not shown) used to deliver the gasket member 12. The valve member 14 may then be secured to the collar 22. For example, as shown in FIG. 5, the valve member 14 may be directed into the recess 23 of the collar 22 such that a lower portion 36 of the frame 32 contacts and directs the tabs 16 radially outwardly. Once the lower portion 36 of the frame 32 passes below the free ends 16*a* of the tabs 16, the tabs 16 may resiliently return inwardly to capture the lower portion 36 below the free ends 16*a*. The inwardly biased tabs 16 thereafter prevent the valve member 14 from moving upwardly, because the lower portion 36 of the frame 32 contacts the tabs 16, thereby securing the valve member 14 to the gasket member 12.

In addition or alternatively, the collar 22 and/or valve member 14 may include other connectors (not shown), e.g., a drawstring, sutures, guide rails, and the like to secure the valve member 14 relative to the collar 22. Exemplary connectors are disclosed in the references incorporated elsewhere herein, e.g., in US Publication Nos. 2006/0195184 and 2006/0235508, or in application Ser. No. 60/746,038, incorporated by reference above.

Optionally, if the collar 22 and frame 32 are generally circular, it may be possible to rotate the valve member 14 within the collar 22. As the valve member 14 is rotated, the lower portion 36 of the frame 32 may simply slide around under the tabs 16. Thus, the valve member 14 may be rotated to a desired angular orientation within the biological annulus 90.

Once the valve member 14 is secured, any tools may be removed, and the procedure completed using known methods.

The collar 22 may support the valve member 14 within a sinus cavity 98 above the biological annulus 90. For example, the spacing of the collar 22 from the annular ring 18 may predispose the valve member 14 within the sinus of Valsalva above an aortic valve site. During implantation, if desired, the valve member 14 may be pressed into the collar 22, whereupon the spring structure 40 may deform, allowing the collar 22 to move axially towards the annular ring 18. When the valve member 14 is released within the sinus cavity 98, the spring structure 40 may resiliently move upwardly away from the biological annulus 90. Thus, the spring structure 40 may be radially soft and flexible, while providing desired axial support for the valve member 14.

Because the valve member 14 is supported within the sinus cavity 98 in this manner, the valve member 14 may be selected from a larger size than the diameter or other cross-section of the biological annulus 90. For example, it may be possible to select a valve member 14 that is at least about two millimeters (2 mm) larger than the annular ring 18 for aortic valve applications. In addition, the valve member 14 and collar 22 may allow blood to flow around the valve member 14, e.g., to enter the coronary arteries or other vessels (not shown) communicating with the sinus cavity 98. Even though the valve member 14 and collar 22 are larger than the annular ring 18 and biological annulus 90, the sinus cavity 98 may be sufficiently large to allow blood to flow around the valve member 14 and collar 22 into the coronary arteries or other vessels adjacent the biological annulus 90.

In addition or alternatively, the sewing ring 20 may have a tri-lobular or other shape (not shown) that may avoid obstructing the coronary arteries or other vessels communicating with the sinus cavity 98. Optionally, the sewing ring 20 may include a stiffening structure, e.g., core 25, to maintain perfusion of the coronary arteries or other vessels communicating with the sinus cavity 98.

If desired, the collar 22 may allow the valve member 14 to be removed from the sinus cavity 98, e.g., to be replaced with a new valve. To remove the valve member 14, a tool may be inserted between the frame 32 and the sidewall 22*b*, e.g., to deflect the tabs 16 radially outwardly. With the tabs 16 deflected outwardly, the lower portion 36 of the frame 32 may be lifted past the tabs 16, allowing the valve member 14 to be removed from the collar 22. Once the valve member 14 is removed, another valve (not shown) may be introduced and received within the collar 22, as desired.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A prosthesis for receiving a prosthetic valve to replace a preexisting natural or prosthetic heart valve within a biological annulus adjacent a sinus cavity, comprising:
   an annular member implantable within a biological annulus for dilating tissue surrounding the biological annulus;
   a collar disposed above the annular member, the collar comprising one or more connectors for securing a prosthetic valve to the collar, and
   a spring structure coupling the collar to the annular member such that collar is movable relative to the annular member, the spring structure comprising a helical member including a first end coupled to the collar and a second end coupled to the annular member.

2. The prosthesis of claim 1, the collar comprising an annular band coupled to the spring structure.

3. The prosthesis of claim 1, the annular member comprising the one or more connectors for securing a prosthetic valve to the collar.

4. The prosthesis of claim 1, the one or more connectors comprising a plurality of detents extending at least partially inwardly from the collar for capturing a portion of a prosthetic valve thereunder.

5. The prosthesis of claim 1, further comprising a sewing ring extending radially outwardly relative to the annular member.

6. The prosthesis of claim 5, the sewing ring comprising a multi-lobular shape.

7. The prosthesis of claim 5, the sewing ring comprising a stiffening structure to maintain perfusion of the coronary arteries.

8. The prosthesis of claim 5, further comprising fabric covering at least a portion of one or more of the annular member, the sewing ring, and the collar.

9. The prosthesis of claim 5, the spring structure being deflectable radially inwardly to at least partially expose the sewing ring to facilitate delivering one or more fasteners into the sewing ring.

10. The prosthesis of claim 1, the collar being biased by the spring structure away from the annular member.

11. The prosthesis of claim 1, the collar being movable along a longitudinal axis towards the annular member.

12. A heart valve assembly, comprising:
    an annular prosthesis implantable within a biological annulus, the annular prosthesis comprising an annular member for delivery into the biological annulus, a sewing ring extending radially outwardly from the annular member, and a collar disposed above the annular member and coupled to the annular member by a spring structure, the collar comprising an annular band coupled to the spring structure; and
    a prosthetic valve comprising a frame securable to the collar.

13. The heart valve assembly of claim 12, wherein the collar includes one or more connectors for securing the prosthetic valve to the annular prosthesis.

14. The heart valve assembly of claim 13, the one or more connectors comprising a plurality of detents extending at partially inwardly from the collar for capturing a portion of the prosthetic valve thereunder.

15. The heart valve assembly of claim 12, wherein the frame comprises one or more ears extending downwardly, and the collar comprises one or more grooves for receiving the one or more ears.

16. The heart valve assembly of claim 12, wherein the prosthetic valve comprises a mechanical valve.

17. The heart valve assembly of claim 12, wherein the prosthetic valve comprises a bioprosthetic valve.

18. The heart valve assembly of claim 12, the spring structure comprising a helical member including a first end coupled to the collar and a second end coupled to the annular member.

19. The heart valve assembly of claim 12, wherein the sewing ring comprises a multi-lobular shape.

20. The heart valve assembly of claim 12, wherein the sewing ring comprises a stiffening structure configured to maintain perfusion of the coronary arteries.

21. The heart valve assembly of claim 12, further comprising fabric covering at least a portion of one or more of the annular member, the sewing ring, and the collar.

22. The heart valve assembly of claim 12, the spring structure being deflectable radially inwardly to at least partially expose the sewing ring to facilitate delivering one or more fasteners into the sewing ring.

23. The heart valve assembly of claim 12, wherein the collar is biased by the spring structure away from the annular member.

24. The heart valve assembly of claim 12, wherein the collar is configured to be movable along a longitudinal axis towards the annular member.

25. The prosthesis of claim 1, wherein the collar comprises one or more grooves for receiving one or more ears on a frame of a prosthetic valve secured to the collar.

* * * * *